United States Patent
Ohta et al.

(12)
(10) Patent No.: US 6,417,224 B1
(45) Date of Patent: Jul. 9, 2002

(54) PROPHYLACTIC, THERAPEUTIC AGENT FOR OSTEOPOROSIS

(75) Inventors: Atsutane Ohta; Masao Hirayama; Takashi Adachi, all of Saitama (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 09/623,747

(22) PCT Filed: Mar. 3, 1999

(86) PCT No.: PCT/JP99/01012

§ 371 (c)(1),
(2), (4) Date: Sep. 5, 2000

(87) PCT Pub. No.: WO99/44621

PCT Pub. Date: Sep. 10, 1999

(30) Foreign Application Priority Data

Mar. 6, 1998 (JP) .............................. 10-55267

(51) Int. Cl.⁷ ................... A61K 31/35; A01N 65/00
(52) U.S. Cl. ................... 514/456; 514/783; 514/26; 514/455; 424/195.1
(58) Field of Search ................ 514/456, 783, 514/26, 455; 424/195.1

(56) References Cited

U.S. PATENT DOCUMENTS 5,043,326 A * 8/1991 Stadler nee Szoke et al. 514/58
5,424,331 A * 6/1995 Shlyankevich ............... 514/456
5,506,211 A * 4/1996 Barnes et al. ................. 514/27
5,569,459 A * 10/1996 Shlyankevich ........... 424/195.1

FOREIGN PATENT DOCUMENTS

| JP | 60-48924 | 3/1985 |
| JP | 62-103077 | 5/1987 |
| JP | 8-231533 | 9/1996 |

OTHER PUBLICATIONS

Arjmandi et al. "Dietry soybean protein prevents bone loss in an ovariectomized rat model osteoporosis." Human and clinical nutrition, pp. 161–167, 1996.*

* cited by examiner

Primary Examiner—Ralph Gitomer
Assistant Examiner—Devesh Khare
(74) Attorney, Agent, or Firm—Flynn, Thiel, Boutell & Tanis, P.C.

(57) ABSTRACT

The prophylactic, therapeutic agent for osteoporosis of the invention is a combination of an indigestible oligosaccharide with phytoestrogen which inhibits bone loss. The action of inhibiting the reduction of bone density can be improved remarkably by combining the indigestible oligosaccharide with phytoestrogen.

3 Claims, No Drawings

PROPHYLACTIC, THERAPEUTIC AGENT FOR OSTEOPOROSIS

TECHNICAL FIELD

This invention relates to a prophylactic, therapeutic agent capable of inhibiting bone loss which is found in osteoporosis.

BACKGROUND ART

In Japan, the population of aged persons is sharply increasing, and various social problems occur therewith. One of the problems is in nursing of the aged persons. Most of the aged persons who require nursing are bedridden, except for persons suffering from cranial nerve troubles, such as dementia. The greatest cause which makes aged persons bedridden is bone fracture caused by osteoporosis. Therefore, it is very important to prevent osteoporosis.

Osteoporosis is caused by trouble in the relationship between resorption and formation of the bone, and various reasons are pointed out, such as metabolic troubles and internal secretion troubles. Various medicines have already been developed.

Estrogen is a female hormone which inhibits resorption of the bone. It has already been used in clinical fields for the medical treatment of osteoporosis and its medical effects have been confirmed. However, its relevance to uterine cancer has been pointed out, and therefore, it cannot be said that it has no problems.

Thereupon, phytoestrogen is being investigated as an alternative. Phytoestrogen is contained in plant, and exhibits female hormone-like action. As representative components thereof, genistein and daidzein are known, which are isoflavons of soybean, and enterolactone and enterodiol are further known, which are lignars contained in rye, blueberry, sesame, tea and so on.

As a result, it has become apparent that phytoestrogen also has the action of inhibiting bone loss, and investigations are advanced for putting it to practical use (Biol. Pharm. Ball., 21(1) 62–66 (1998), J. Nutr. 126: 161–167, 1996, J. Nutr. 126: 176–182, 1996). However, its effects are still insufficient.

An object of the invention is to provide an agent which prevents the reduction of bone density occurring with the outbreak and progress of osteoporosis and exhibits excellent effects for the prevention and medical treatment of osteoporosis.

DISCLOSURE OF INVENTION

The inventors investigated eagerly in order to achieve the above object, and as a result, they found that the reduction of bone density can be improved remarkably by combining an indigestible oligosaccharide, such as fructooligosaccharides, with phytoestrogen.

The present invention has been made based on this finding, and relates to a prophylactic, therapeutic agent for osteoporosis which comprises phytoestrogen and an ingestible oligosaccharide.

Although the function and mechanism are not entirely clear, it can be assumed that enteric bacteria, such as Bifidobacterium bifidum having a high β-glucosidase activity, are increased by the intake of the indigestible oligosaccharide, and absorption of phytoestrogen is raised thereby steadily. That is, natural phytoestrogen is combined with a sugar chain to form a glycoside, and its absorption by an organism is not possible until the sugar chain is cut off. The cutting off of the sugar chain is made mainly by bacteria existing in the large intestine. However, the type and quantity of the bacteria greatly differ between individuals, and in some persons, the absorption hardly occurs. It can be considered that enteric bacteria are increased or their activities are raised by the combination of the indigestible oligosaccharide, and the sugar chain is cut off phytoestrogen at a high rate to raise the absorption rate of phytoestrogen.

BEST MODE FOR CARRYING OUT THE INVENTION

Phytoestrogen is contained in plant, and exhibits female hormone-like action. The phytoestrogen is a substance called SERM (Selective estrogen receptor modulator) contained in plants, and exhibits a similar action to female hormones in an organ specificity viewpoint, such as interacting with a receptor of estrogen which is a female hormone and inhibiting resorption of the bone. The phytoestrogen is an isoflavon, such as genistein or daidzein, which are isoflavons of soybean, a lignan, such as enterolactone or enterodiol, or the like. Plants containing phytoestrogen in quantity are soybean, rye, blueberry, sesame, tea and so on. The phytoestrogen applicable to the prophylactic, therapeutic agent for osteoporosis of the invention may be in a form of the above food itself or a fabricated one thereof as well as an extracted semipurified one.

The indigestible oligosaccharide is a disaccharide to pentacontasaccharide, preferably a disaccharide to pentasaccharide, which is not digested by the digestive enzymes in an organism, and preferred ones increase absorption of calcium in the intestines. Preferable examples are fructooligosaccharides, raffinose, galactooligosaccharides, xylooligosaccharides and the like. The fructooligosaccharides are a designation of a mixture of sugars having a similar structure to sucrose which are formed by bonding 1 to 3 fructose molecules to the fructose residue of sucrose. Each sugar is named 1-kestose ($GF_2$), nystose ($GF_3$) and fructo-furanosyl nystose ($GF_4$) from the shortened chain length one. The galactooligosaccharide is a generic term for 2 to 6 sugar oligosaccharides formed by reacting β-galactosidase with lactose (disaccharide composed of galactose and glucose bonded by a β-1,4-bond). A representative component of the galactooligosaccharide is 4'-galactosyl lactose (hereinafter abbreviated as 4'-GL) having a structure composed of lactose and galactose bonded through a β-1,4-bond. As the other components, there are tetra to hexasaccharides formed by further bonding galactose molecule(s) to 4'-GL through β-1,4-bond(s), disaccharides composed of galactose and glucose bonded through a β-1,3-bond, and so on. The structure of the galactooligosaccharide is shown below:

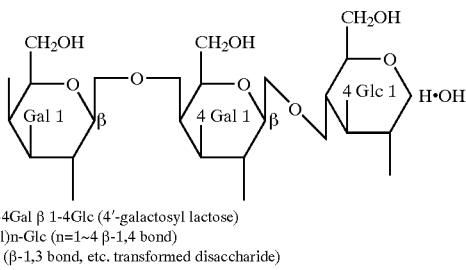

Gal β 1-4Gal β 1-4Glc (4'-galactosyl lactose)
Gal-(Gal)n-Glc (n=1~4 β-1,4 bond)
Gal-Glc (β-1,3 bond, etc. transformed disaccharide)

The xylooligosaccharide is a sugar derived from hemicellulose having a structure composed of about 2 to 7 xylose molecules bonded through β-1,4-bond(s). Some xylooligosaccharides have a side chain of arabinose, glucuronic acid, etc. The indigestible oligosaccharide may be a crude product as well as a purified one.

A suitable content ratio of phytoestrogen and the indigestible oligosaccharide is about 1:10 to 1:1,000, preferably about 1:100 to 1:500.

The prophylactic, therapeutic agent of the invention may not contain calcium.

The prophylactic, therapeutic agent of the invention is taken orally, and a suitable unit ingestion is about 1 to 100 mg, preferably about 10 to 50 mg as the weight of phytoestrogen per 1 kg of body weight.

EXAMPLES

Example 1

The prophylactic, therapeutic effects of the invention on osteoporosis were evaluated using ovariectomized female rats which are commonly used as a model animal for osteoporosis (reference: Nippon Eiyo Shokuryo Gakkai-shi, vol. 43, No. 6, pp 437–443). That is, 20 SD strain female rats of 15 weeks old were divided into 5 groups each consisting of 4 rats. The ovaries of the rats of 4 groups were removed, and a counterfeit operation was applied to the remaining one group, under ether anesthesia, respectively. The test feed shown in Table 1 was fed to the rats of each group. In this example, soybean flour containing isoflavon in quantity (containing 2.6 mg isoflavon per 1 g soybean flour, reference: Shokuhin to Kaihatsu, Vol. 31, No. 6 pp 44–47, 1996) was used as phytoestrogen. Pure fructooligosaccharides was used having a purity of 95 wt. % or more (trade name: "Mei-Oligo-P Powder, Meiji Seika Kaisha, Ltd."). Using the above soybean flour and fructooligosaccharides, a standard purified feed (control feed), a fructooligosaccharides-containing feed, a soybean flour-containing feed, and a fructooligosaccharide-soybean flour mixture-containing feed, which is the prophylactic, therapeutic agent for osteoporosis of the invention, having a composition described in Table 1 were prepared, and the rats were bred for one month using these feeds. When breeding was finished, the rats were slaughtered and dissected, and the right femur was taken out. After removing the soft tissues, the bone density (BMD) of the femur taken out was measured by a double X-ray bone density measuring apparatus (made by Aroka). The results shown in Table 2 indicate that a remarkable increase of bone density was not found in the case of taking fructooligosaccharide or soybean flour alone compared with the bone density of the counterfeit operation group. However, the reduction of bone density was inhibited remarkably in the group taking the prophylactic, therapeutic agent for osteoporosis of the invention, which is a mixture of both materials, and the bone density was in a similar degree to the bone density of the counterfeit operation group. From the above results, it was confirmed that the agent of the invention is effective for the prophylaxis and medical treatment of osteoporosis.

TABLE 1

Feed Composition (%)

| | Control Feed | Soybean flour feed | Fructooligosaccharides feed | The agent of the invention containing feed |
|---|---|---|---|---|
| Casein | 25 | 22.5 | 25 | 22.5 |
| Corn starch | 49.6 | 49.5 | 49.5 | 49.5 |
| Corn oil | 6 | 6 | 6 | 6 |
| Vitamin mixture | 1 | 1 | 1 | 1 |
| Mineral mixture | 3.5 | 3.5 | 3.5 | 3.5 |
| Cellulose powder | 5 | 5 | 5 | 5 |
| Sucrose | 10 | 10 | 8 | 8 (Prophylactic of the invention) |
| Soybean flour (*1) | 0 | 2.5 | 0 | 2.5 |
| Fructooligosaccharides | 0 | 0 | 2 | 2 |

(*1): 1 g of the soybean flour used in the example contains 2.6 mg soybean isoflavon.

TABLE 2

Bone Density of Rat Femur

| | Femur Bone Density (mg/cm$^2$) | Significant difference from control group (level of significance: p) | Significant difference from Ovariectomized group (level of significance: p) |
|---|---|---|---|
| Control group (counterfeit operation) | 156 | | $p < 0.01$ |
| Ovariectomized group | 147 | $p < 0.01$ | |
| Ovariectomized + fructooligosaccharide group | 150 | $p - 0.05$ | NS |
| Ovariectomized + soybean flour group | 149 | $p < 0.05$ | NS |
| Ovariectomized + prophylactic of the invention group (fructooligosaccharide + soybean flour) | 156 | NS | $p < 0.01$ |

NS: No significant difference

INDUSTRIAL APPLICABILITY

By taking orally the prophylactic, therapeutic agent of the invention, it is possible to inhibit the reduction of bone density and to prevent and remedy osteoporosis. The prophylactic, therapeutic agent of the invention is effective not only for humans but also other animals, such as domestic animals and pets.

The prophylactic, therapeutic agent of the invention can be eaten as it is, drunk by suspending it in a suitable drink or eaten by adding it to a suitable food.

What is claimed is:

1. A prophylactic, therapeutic agent for osteoporosis which comprises phytoestrogen and a fructooligosaccharide.

2. The prophylactic, therapeutic agent for osteoporosis as set forth in claim 1, wherein the content ratio of phytoestrogen and fructooligosaccharide is 1:10 to 1:1000 by weight ratio.

3. The prophylactic, therapeutic agent for osteoporosis as set forth in claim 1 wherein the phytoestrogen is isoflavon.

* * * * *